United States Patent [19]

Pieters et al.

[11] 4,060,499
[45] Nov. 29, 1977

[54] COPPER CHLORIDE/BORON NITRIDE CATALYST FOR SUBSTITUTION CHLORINATION

[75] Inventors: Wim J. M. Pieters, Morristown; Emery J. Carlson, Chatham; Guido P. Pez, Boonton, all of N.J.

[73] Assignee: Allied Chemical Corporation, Morris Township, N.J.

[21] Appl. No.: 761,561

[22] Filed: Jan. 24, 1977

[51] Int. Cl.$^2$ .................. B01J 21/00; B01J 27/06; C07C 17/00
[52] U.S. Cl. .................. 252/432; 252/441; 260/658 R
[58] Field of Search .................. 252/432, 438, 441

[56] References Cited

U.S. PATENT DOCUMENTS

| | | | |
|---|---|---|---|
| 3,210,431 | 10/1965 | Engel | 252/441 X |
| 3,406,211 | 10/1968 | Tiganik et al. | 252/432 X |
| 3,630,889 | 12/1971 | Arey et al. | 252/438 X |

OTHER PUBLICATIONS

Australian Journal of Chemistry, vol. 9, 1956, pp. 206–211, "New Molecular Compounds of the Layerlattice Type".

*Primary Examiner*—Patrick P. Garvin
*Assistant Examiner*—William G. Wright
*Attorney, Agent, or Firm*—Robert A. Harman; Jay P. Friedenson

[57] ABSTRACT

A catalyst consisting essentially of cuprous chloride intercalated in crystalline boron nitride, containing at least 10% copper, useful for substitution chlorination of organic substances in vapor phase at elevated temperature by action of chlorine or HCL and oxygen. Highly selective for chlorination versus oxidation and hydrolysis even at high conversions, using partially chlorinated organic material as reactant, in particular methyl chloride.

3 Claims, No Drawings

COPPER CHLORIDE/BORON NITRIDE CATALYST FOR SUBSTITUTION CHLORINATION

BACKGROUND OF THE INVENTION

This invention relates to compositions useful as catalysts for vapor phase substitution chlorination of partially chlorinated organic materials by action of chlorine, or hydrogen chloride, and elemental oxygen in vapor phase at elevated temperature.

Such catalyzed reactions are broadly known. Illustrative is U.S. Pat. No. 3,210,431 of Oct. 5, 1965 to W. F. Engel. This patent discloses the substitution chlorination of saturated aliphatic and cycloaliphatic hydrocarbons and alkenes and aromatic hydrocarbons by reacting them with hydrogen chloride and oxygen or oxygen-containing gases in the presence of catalysts; for example, chlorides of copper and rare earth metals supported on silica gel, preferably; or on pumice. Copper content is generally 1 to 20% by weight. Temperatures disclosed in the patent are in the range from 100° to 650° C. According to that invention, the catalyst composition contains in addition to cupric chloride, the chlorides of one or more rare earth metals and one or more alkali metals. The patent states that by use thereof, relatively low temperatures, for example, 100°–300° C. can be employed. The advantages recited are that the copper chloride hardly or not at all volatilizes and there is hardly any corrosion; moreover, chlorinations of, in particular, alkenes proceed with high selectivity and the process can be carried out in a fluidized catalyst bed. The specific working examples show only ethylene as the hydrocarbon and only addition chlorination, not substitution chlorination.

Also known in the prior art is the formation of so-called intercalated compositions wherein various metal chlorides are heated at temperatures such as 100° to 400° C. with crystalline boron nitride, whereby a composition is formed in which the metal chloride is held by some such means as electronic interaction or coordination of cations within the layers of boron nitride crystals. (R. C. Croft, *Australian Journal of Chemistry*, volume 9 of 1956, pages 206–211.) Using specifically cuprous chloride at 400° C. the percent of CuCl found in the boron nitride after washing was 5%, i.e. about 3.2% of copper.

SUMMARY OF THE INVENTION

In accordance with the present invention, the catalyst for the subject chlorination is a composition consisting essentially of at least 10% by weight of copper, as the chloride, intercalated in boron nitride. A certain minimum activity for the subject chlorination is important, sufficient to outweigh oxidation by elemental oxygen acting on the organic material. In general the catalyst activity increases with copper content. The catalyst is used in particular in the process for production of more highly chlorinated methanes by bringing at least one partially chlorinated methane, in vapor phase at elevated temperature, into contact with the catalyst, together with elemental chlorine, or hydrogen chloride, and elemental oxygen and permissibly also inert gas. More particularly, the temperatures used are about 350° to 500° C. and the residence times, based on 50% of the catalyst bed volume being void space, are generally in the range of about 0.1 to 5 seconds.

The process for producing such catalyst composition comprises heating copper chloride and boron nitride in weight ratio in the range of about 0.3:1 to 10:1, calculated as cuprous chloride, at a temperature in the range of about 550° to 800° C. in an inert environment, maintained dry and substantially free of oxygen, e.g. by flowing dry inert gas through the heating chamber. When copper chloride is referred to herein as being heated, it is to be understood that the starting copper chloride can be either cuprous or cupric and if cupric chloride is thus heated, it is thereby converted to cuprous chloride. The intercalated copper of our catalyst is in the cuprous state.

DESCRIPTION OF THE PREFERRED EMBODIMENTS

Our catalyst in its preferred embodiment has a copper content of about 25% – 40% by weight. A partially chlorinated methane is a preferred reactant illustrative of those usable in our process. In the inlet reaction mixture in such preferred process, the partially chlorinated reactant is principally methyl chloride; and the balance of the inlet reaction mixture, other than inert gases if present, consists essentially of at least about the stoichiometrically required proportions of hydrogen chloride and elemental oxygen to produce the desired chlorination product, i.e. dichloromethane, chloroform, or tetrachloromethane and water from the methyl chloride and hydrogen chloride; but not over about a 5-fold excess of said hydrogen chloride or said oxygen. The particular advantage of our catalyst in such process is that the catalyst is highly stable against volatilization of the copper chloride ingredient even at very high temperatures such as 800° C. and therefore shows good life and very low corrosive action. This catalyst is very highly selective for chlorination of methyl chloride as against oxidation thereof. In particular, products very rich in tetrachloromethane can be obtained by its use, with relatively little hydrolysis or oxidation side reactions.

The copper chloride constituent of our catalyst can be supplemented by other metal chlorides such as alkali metal chlorides, rare earth metal chlorides, and aluminum chloride; but these are not necessary for good results and may even, in some cases, interfere with the intercalation of copper chloride in the catalyst.

There follow specific examples illustrative of the invention and setting forth the best mode contemplated by us for carrying out the invention; these examples are to be understood as illustrative and not as limiting.

PREPARATION OF CATALYSTS

Catalyst "A"

A mixture of 7 gm. of powdered boron nitride and 28 gm. of powdered reagent grade cuprous chloride was blended by rolling in a closed container for 2 hours. A 5.24 gm. portion of the blend was allowed to react for 60 hours at 700°–750° C in a horizontal "Vycor" fused silica glass tube, housed in a tube furnace, and fitted for flowing therethrough a stream of dry nitrogen which was introduced at the rate of 50 cc per minute. Upon cooling, the composition was washed repeatedly with a solution of 5% HCl to remove free copper chloride, washed with water, and dried. By analysis the composition contained 32.6% by weight of copper, corresponding by calculation to weight ratio of about 1:1 of cuprous chloride:boron nitride. The product was a free-flowing powder of apparent bulk density about 0.4 gm./ml. and surface area about 10 sq. meters/gm. by the BET method using nitrogen gas.

Catalyst "B"

This catalyst was prepared by the method used for Catalyst "A" above, except that the batch size was 11.91 gm. instead of 5.24 gm.; the heating time of the batch was 28 hours instead of 60 hours; and the temperature of heating the batch was 600°–625° C instead of 700°–750° C. The product had apparent bulk density of about 0.5 gm./ml. and surface area about 10 sq. meters/gm.

CATALYST EVALUATIONS

Catalysts "A" and "B" prepared as above were used in oxyhydrochlorination runs with methyl chloride, as summarized in the table below under "A" and "B" respectively.

The reactor used consisted essentially of a vertical open ended quartz tube, surrounded by a jacket, and supported in an electrically heated furnace. Reactant gases are supplied through inlet valves and pass out through exit valves. The valves are thermally controlled by a temperature controller; so as to pass the reactants through the apparatus at a programmed series of temperatures. The jacket is sealed to the inner tube near the top of that tube and closes over below the open bottom end of the reactor tube. The catalyst bed is retained in the reactor by quartz fiber plugs.

The reactant gases enter the jacket through a side arm, flow down the annules between the jacket and the inner tube to the closed off bottom of the jacket, rise from there into the open end of the reactor tube, pass through the catalyst bed therein, and exit from the top of the reactor tube.

The exit manifold delivers reactants to product separating chromatographic columns and associated detectors, and then to an outlet. The flows of the reactant gases (HCl, $O_2$, $CH_3Cl$) and of diluent gas $N_2$ are set and regulated by electronic flow controllers. Total pressure of the combined reactant mixture is recorded by a pressure recorder ahead of the inlet.

Carrier gas helium for the analyses is controlled by a pressure regulator and diverted to the chromatographic columns by another valve.

The headings of the table below are explained as follows, where [ ] represents mols concentration per 100 mols of the inlet reactants (i.e. $CH_3Cl$, $O_2$ and HCl) and [CM] represents total mols of chlorinated methane products per 100 mols of reactants.

"Res. Time" (residence time) = (catalyst void space)/(inlet gas flow rate at reaction temperature), where catalyst void space is taken as 50% of the volume of the catalyst bed.

"$CH_3Cl$ Conv." (conversion) = 100 [$CH_3Cl$]in − [$CH_3Cl$]out/[$CH_3Cl$]in.

"Selec." (selectivity) = 100 [CM]/[$CH_3Cl$]in − [$CH_3Cl$]out

TABLE

| | Res. Time Sec | Temp. °C | Inlet | | | Exit | | | | | |
|---|---|---|---|---|---|---|---|---|---|---|---|
| | | | $O_2$ % | $CH_3Cl$ % | HCl % | $CH_3Cl$ Conv% | Selec. % | $CH_3Cl$ % | $CH_2Cl_2$ % | $CHCl_3$ % | $CCl_4$ % |
| Catalyst "A" | 2.28 | 435 | 33.9 | 7.40 | 58.7 | 98 | 93.1 | .15 | .13 | 2.01 | 3.37 |
| | 2.31 | 425 | 33.6 | 7.02 | 59.4 | 87 | 98.2 | .91 | 1.65 | 3.52 | .70 |
| | 2.33 | 418 | 33.2 | 6.70 | 60.1 | 78 | 99.5 | 1.52 | 2.91 | 2.06 | .15 |
| | 2.36 | 410 | 33.0 | 6.36 | 61.6 | 48 | 99.8 | 3.28 | 3.00 | .02 | .02 |
| | 2.39 | 400 | 32.5 | 5.70 | 61.8 | 48 | 99.8 | 2.93 | 2.69 | .02 | .02 |
| "B" | 3.0 | 398 | 29.5 | 18.9 | 51.6 | 79 | 72.5 | 3.92 | 4.80 | 2.64 | .60 |
| | 3.0 | 390 | 29.5 | 18.5 | 52.0 | 54 | 87.0 | 8.52 | 6.61 | 2.01 | .00 |

As can be seen from the foregoing table, the selectivity of the substitution chlorination of methyl chloride, versus oxidation, is well over 90% even at high conversion such as 98% when using about a 2- to 3-fold excess of HCl and oxygen over the stoichiometric proportions for conversion of the methyl chloride to carbon tetrachloride and water. At lower conversions in the range of 50% – 80% the selectivity using these proportions of reactants approaches 100%.

Moreover, by thermogravimetric analysis this type of catalyst has been found to be stable against loss of weight up to at least 800° C.

The high selectivity for substitution chlorination of methyl chloride and its chlorination products is believed to be due to the following facts. The active catalyst is intercalated, i.e. held in the relatively narrow interplanar space between adjoining layers of the boron nitride crystals; and is strongly held there so as not to volatilize into the vapor phase. Thus the methyl chloride and its chlorination products contact chlorine and oxygen in the vapor phase but being relatively bulky, the chloride and chlorination products cannot contact the intercalated copper chloride, which acts almost exclusively to form chlorine from the hydrogen chloride and oxygen present. Moreover, the boron nitride support is inert in tests for acidic sites; conformably therewith, it exerts little or no catalytic action toward hydrolysis of the chloromethanes.

The same activity as with methyl chloride can be expected with any chlorinatable organic material, stable in vapor phase in presence of oxygen at elevated temperature and containing hydrogen replaceable by chlorine under vapor phase reaction conditions (up to 800° C.); and of at least the molecular size of methyl chloride. Specifically, the present catalyst can be used for oxychlorination and oxyhydrochlorination of monochloroethane, and of propane and butanes.

It is evident in view of the foregoing that our catalyst can be used generally for reactions involving conversion of HCl by elemental oxygen to chlorine, especially such reactions involving also vapor phase substitution chlorination of partially chlorinated organic materials, wherein hydrogen is replaced by chlorine forming hydrogen chloride which is then oxidized to chlorine and water. In such reactions elemental chlorine in the vapor phase can evidently be substituted for part or all of the hydrogen chloride reactant referred to in the foregoing. Such substitution chlorination by chlorine, in presence of oxygen, replacing hydrogen in an organic molecule with ultimate formation of water is known as "oxychlorination"; and the above discussed substitution chlorination process, using hydrogen chloride as initial reactant together with oxygen, is known as "oxyhydrochlorination."

We claim:

1. Composition useful as catalyst for substitution chlorination of partially chlorinated organic material by action of elemental chlorine, or hydrogen chloride, and elemental oxygen in vapor phase at elevated temperature, which composition consists essentially of at least 10% by weight of copper, as cuprous chloride, intercalated in boron nitride.

2. Composition of claim 1 wherein the copper content is about 25% – 40% by weight.

3. Process for producing the composition of claim 1, which process comprises heating copper chloride and boron nitride in weight ratio in the range of about 0.3:1 to 10:1, calculated as cuprous chloride, at a temperature in the range of about 550° to 800° C. in an inert environment, maintained dry and substantially free of oxygen.

* * * * *